US012766026B2

(12) United States Patent
Badr

(10) Patent No.: US 12,766,026 B2
(45) Date of Patent: Oct. 20, 2026

(54) NECK BRACE AND SUPPORT FOR PREVENTION OF OBSTRUCTIVE SLEEP APNEA

(71) Applicant: Portege Enterprises LLC, Plano, TX (US)

(72) Inventor: Adnan S. Badr, Plano, TX (US)

(73) Assignee: Portege Enterprises LLC, Plano, TX (US)

(*) Notice: Subject to any disclaimer, the term of this patent is extended or adjusted under 35 U.S.C. 154(b) by 0 days.

(21) Appl. No.: 19/449,581

(22) Filed: Jan. 15, 2026

(65) Prior Publication Data

US 2026/0144666 A1 May 28, 2026

(51) Int. Cl.
*A61F 5/37* (2006.01)

(52) U.S. Cl.
CPC .................................. *A61F 5/3707* (2013.01)

(58) Field of Classification Search
CPC ...... A61F 5/055; A61F 5/56; A61F 2005/563; A61F 5/05883; A61F 5/05891; A47G 9/1081; A61G 7/1084
See application file for complete search history.

(56) References Cited

U.S. PATENT DOCUMENTS 3,306,284 A 2/1967 McKinley
5,005,563 A * 4/1991 Veale ...................... A61F 5/055 602/18
5,385,535 A 1/1995 McGuinness
5,624,387 A * 4/1997 McGuinness ........... A61F 5/055 602/17
6,423,020 B1 7/2002 Koledin
7,789,843 B2 9/2010 Ray
8,950,027 B2 2/2015 Yamamoto et al.
10,117,768 B1 11/2018 Freed et al.
2007/0256694 A1 11/2007 Kussick
2008/0223377 A1 9/2008 Kussick
2010/0224198 A1 9/2010 Ayuse et al.
2010/0307512 A1* 12/2010 Krook ....................... A61F 5/56 128/848
2021/0378858 A1 12/2021 Urmey
2022/0054300 A1* 2/2022 Vaidya ...................... A61F 5/56
2024/0423826 A1 12/2024 Kohler
2026/0053656 A1* 2/2026 Jiang ....................... A61F 5/055

FOREIGN PATENT DOCUMENTS

WO WO 2011/102661 A2 8/2011
WO WO 2017/115266 A1 7/2017

* cited by examiner

*Primary Examiner* — Kari K Rodriquez
(74) *Attorney, Agent, or Firm* — Michael J. Feigin, Esq.; Feigin and Fridman LLC

(57) ABSTRACT

A sleep apnea device for positioning the neck and jaw of a user, the device including a skeletal structure and a cushioning structure. The skeletal structure includes a lower section, an upper section including at least one support, and a plurality of longitudinal rods. The cushioning structure includes a rear portion and side portions, and defines at least one cavity, a plurality of longitudinal bores, and an upper surface. The lower section of the skeletal structure is disposed within the cavity of the cushioning structure, and the upper section of the skeletal structure is disposed above the upper surface of the cushioning structure. Each longitudinal rod in the plurality of longitudinal rods extends through a corresponding one of the plurality of longitudinal bores to connect the upper section with the lower section of the skeletal structure.

9 Claims, 18 Drawing Sheets

NECK BRACE AND SUPPORT FOR PREVENTION OF OBSTRUCTIVE SLEEP APNEA

FIELD OF THE DISCLOSED TECHNOLOGY

The disclosed technology relates generally to a medical device for treatment of obstructive sleep apnea. More specifically, the disclosed technology relates to a hybrid neck brace and neck support device that positions the lower jaw, neck, and/or head, thereby to position the tongue to ensure clear access of the airway of the user.

BACKGROUND OF THE DISCLOSED TECHNOLOGY

Obstructive sleep apnea (OSA) is a condition mainly characterized by loud snoring and repeated brief episodes of interrupted breathing during sleep, and affects at least one billion people globally. Obstructive sleep apnea occurs when the muscles in the back of the throat fail to keep the airway open, making it difficult to breathe. It is more common in people who are overweight, but it can affect anyone. For example, some small children may have obstructive sleep apnea due to enlarged tonsil tissue in their throats.

For those with OSA, the airway collapses or becomes blocked during sleep, which causes shallow breathing, or pauses in breathing, leading to fragmented sleep and low blood oxygen levels. Such collapsing of airways is referred to as Upper Airway Restrictive Syndrome (UARS) and may also occur from medical conditions such as deviated septum, large turbinates, narrow palate, long soft palate etc.

Some patients with obstructive sleep apnea may benefit from surgery. The type of surgery depends on the cause of the sleep apnea. Examples for common types of surgical procedures for sleep apnea include removing the tonsils and adenoids, if these organs are blocking the airway. This can be especially helpful in the case of children. In advanced, non-responsive cases, the mandible may be broken and lengthened, to move the tongue out of the throat region.

Another common treatment for sleep apnea, which does not require invasive surgery, is called continuous positive airway pressure (CPAP). In this treatment, during sleeping, the patient wears a special mask over nose and mouth. The mask is connected by a hose to a machine that provides pressurized air. The system keeps the wearer's airway open by increasing the air pressure breathed in by the wearer. However, such masks cover a large portion of the face and head, are generally uncomfortable, and may leak or fall off, thus reducing effectiveness. Furthermore, such systems are abrasive on the nasal cavity, often causing excessive dryness and discomfort to the user.

Various dental and oral devices have been proposed for treating sleep apnea. Some dental devices advance the lower jaw (mandible) forward, thus adjusting the location of the base of the tongue so it does not obstruct the airway. Other devices are tongue stabilizing devices that force the tongue to remain in a fixed position relative to the lips, also resulting in the tongue being moved forward. Such devices are often uncomfortable and/or unhygienic. The devices must be sterilized regularly to avoid buildup of oral bacteria, and often trigger excess salivation, causing users discomfort by drooling. Furthermore, when the device maintains the mouth partially open, this may cause dryness, potentially leading to other oral problems and/or gum disease.

Positional pillows have also been used for treatment of sleep apnea, for example by elevating the head and upper body. Often, such pillows are used in combination with other devices, such as CPAP systems or oral devices. However, positional pillows are highly prone to user error, for example the user rolling over or pushing the pillow aside during the night, thereby reducing or eliminating the effect of the pillow in improving the user's sleep.

Some braces that cause jaw thrust (advancement of the mandible) and/or head and chin lift are available on the market, such as various collars and neck braces. However, these devices are often very uncomfortable for the user.

Other approaches treat sleep apnea by opening the airway. An uvulectomy is a type of surgery that removes only the uvula. Uvulopalatopharyngoplasty (UPPP) is more extensive, removing the uvula plus part of the soft palate and sometimes the tonsils and adenoids. Inspire therapy uses an implantable device within the chest. Connected wires stimulate the hypoglossal nerve to keep the tongue forward during sleep, preventing airway collapse.

Thus, while there are many different ways of attempting to alleviate problems associated with OSA, there is still room for improvement. There is a need in the art for a device that supports the user's neck while at the same time pushing forward the mandible, which device is comfortable and reliable for use.

SUMMARY OF THE DISCLOSED TECHNOLOGY

Embodiments of the disclosed technology relate generally to medical devices for treatment of obstructive sleep apnea, and more specifically to a hybrid neck brace and neck support device that positions the lower jaw, neck, and/or head to ensure clear access of the airway of the user.

In accordance with embodiments of the disclosed technology, there is provided a sleep apnea device for positioning the neck and jaw of a user. The device includes a skeletal structure and a curved cushioning structure. The skeletal structure includes a lower section, an upper section including at least one support, and a plurality of longitudinal rods. The cushioning structure includes a rear portion and side portions, and defines at least one cavity, a plurality of longitudinal bores, and an upper surface. The lower section of the skeletal structure is disposed within the at least one cavity of the cushioning structure, and the upper section of the skeletal structure is disposed above the upper surface of the cushioning structure. Each longitudinal rod in the plurality of longitudinal rods extends through a corresponding one of the plurality of longitudinal bores to connect the upper section of the skeletal structure with the lower section of the skeletal structure.

In some embodiments, the lower section includes a pair of base portions connected to each other by a rear strip, the base portions and the rear strip being disposed within the at least one cavity of the cushioning structure, each of the base portions including a seat for a lower end of at least one of the plurality of rods.

In some embodiments, the at least one cavity comprises a longitudinal cavity defined in each of the side portions of the cushioning structure and a slit defined in the rear portion of the cushioning structure, each longitudinal cavity accommodating one of the base portions and the slit accommodating the rear strip.

In some embodiments, the plurality of longitudinal bores in the cushioning structure extend between the longitudinal cavities and the upper surface of the cushioning structure.

In some embodiments, the upper section includes a pair of supports, each including a body and a support shelf extending inwardly from the body and adapted to support the jaw of the user, and a pair of jaw-pushing elements, each associated with one of the supports and movable relative thereto. In some embodiments the jaw-pushing elements are adapted, when the device is worn around the neck of the user, to cup the jaw of the user and to position the jaw relative to the neck of the user to improve air flow during sleep.

In some embodiments, a connection between the plurality of longitudinal rods and the upper section of the skeletal structure is adjustable to modify an angle of the upper section relative to the lower section of the skeletal structure such that, when the device is worn around the neck of the user, the neck of the user is extended to improve air flow during sleep.

In accordance with embodiments of the disclosed technology, there is provided a method of treating obstructive sleep apnea using the device of the disclosed technology. The method includes placing the cushioning structure around the neck of the user, placing the mandible within the jaw-pushing elements, and adjusting a position of the jaw pushing elements relative to the corresponding supports, to ensure that the mandible is pushed forward and pulls the tongue away from the user's throat.

In some embodiments, the method further includes adjusting an angle of the supports relative to the upper surface of the cushioning structure to ensure that the mandible is lifted upward and the neck of the user is extended to increase the space in the throat.

DETAILED DESCRIPTION OF EMBODIMENTS OF THE DISCLOSED TECHNOLOGY

A sleep apnea device for positioning the neck and jaw of a user, the device including a skeletal structure and a cushioning structure. The skeletal structure includes a lower section, an upper section including at least one support, and a plurality of longitudinal rods. The cushioning structure includes a rear portion and side portions, and defines at least one cavity, a plurality of longitudinal bores, and an upper surface. The lower section of the skeletal structure is disposed within the cavity of the cushioning structure, and the upper section of the skeletal structure is disposed above the upper surface of the cushioning structure. Each longitudinal rod in the plurality of longitudinal rods extends through a corresponding one of the plurality of longitudinal bores to connect the upper section with the lower section of the skeletal structure.

Embodiments of the disclosed technology will become clearer in view of the foregoing description of the figures. Before delving into the figures, it should be understood that "top," "bottom," "lower," "upper," "front," and "back" are directional terms relative to the typical order of placement of components of the treatment device relative to one another and their orientation relative to the user's body. Thus, the "upper portion" fits closer to the user's head than the "lower portion", "front" refers to the side near the user's face, and so forth.

Figure 1A:
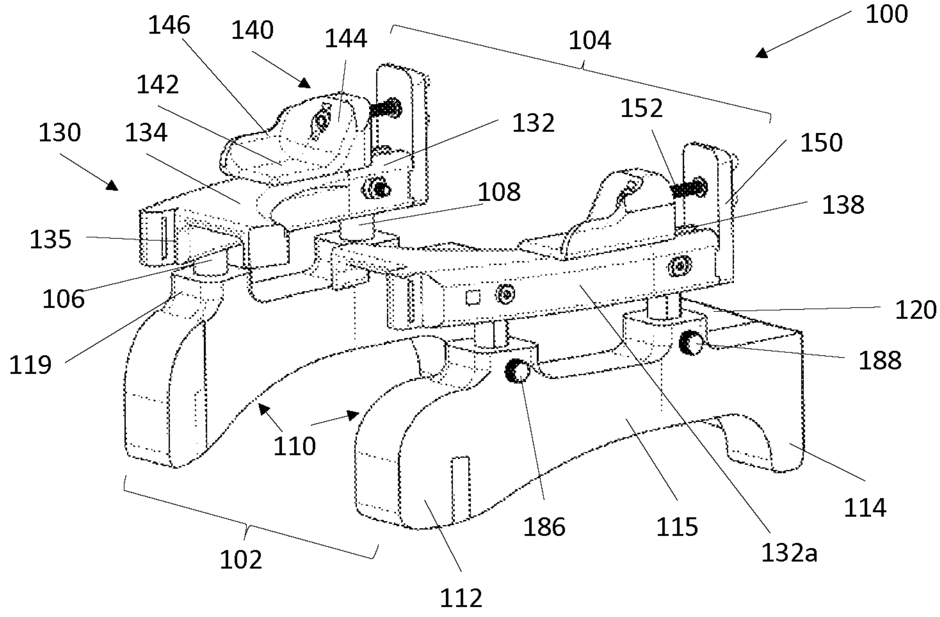
FIG. 1A is a perspective view illustration of a skeletal structure of a sleep-apnea treatment device according to an embodiment of the disclosed technology.
Figure 1B:
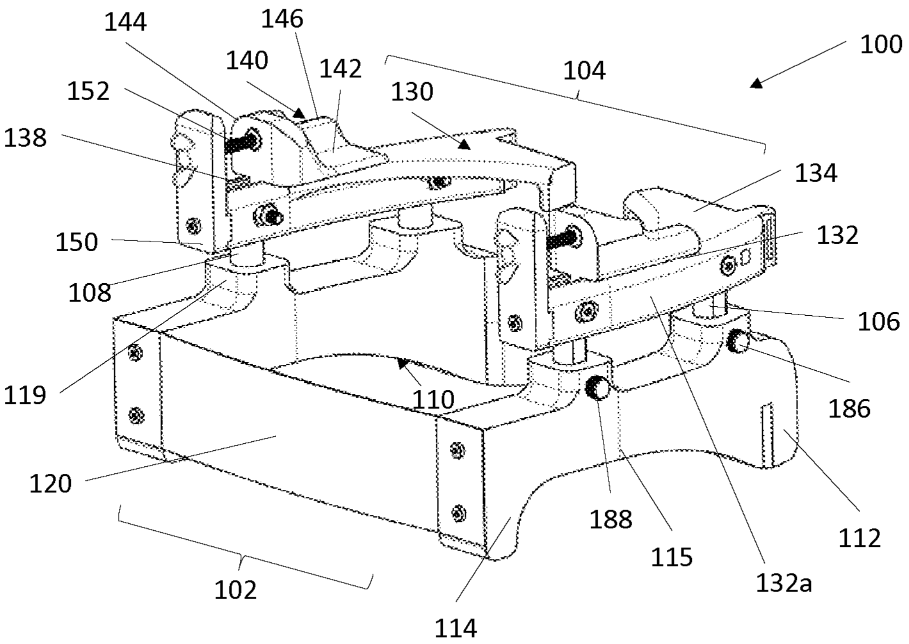
FIG. 1B is a back perspective view illustration of the skeletal structure of FIG. 1A.
Figure 2A:
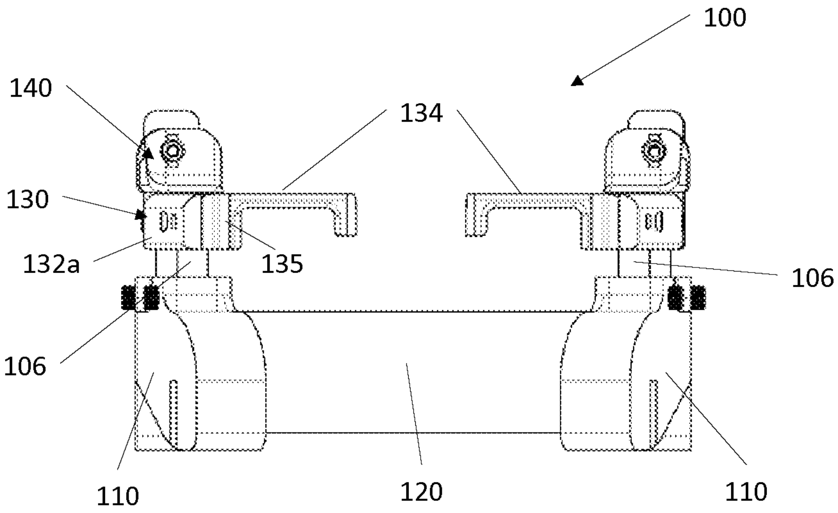
FIG. 2A is a front view planar illustration of the skeletal structure of FIGS. 1A-1B.
Figure 2B:
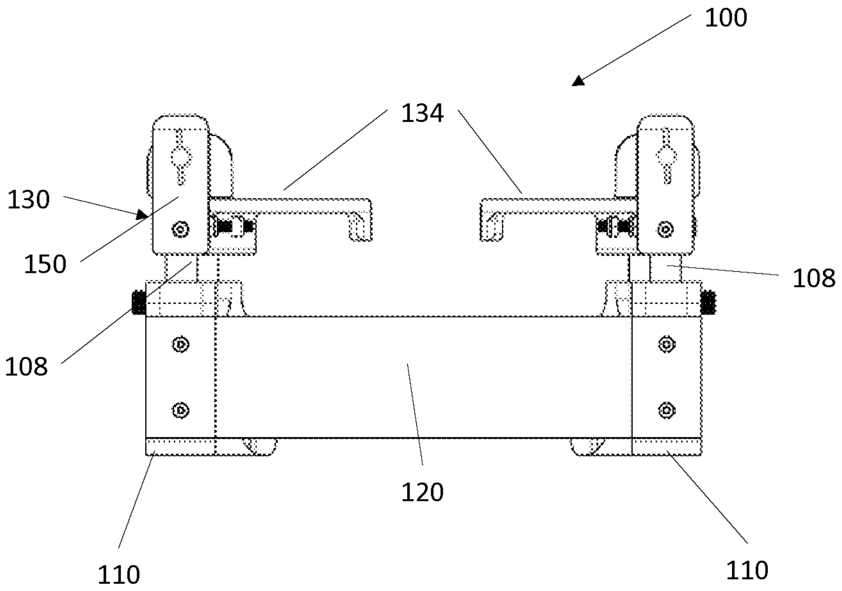
FIG. 2B is a back view planar illustration of the skeletal structure of FIGS. 1A-1B.
Figure 2C:
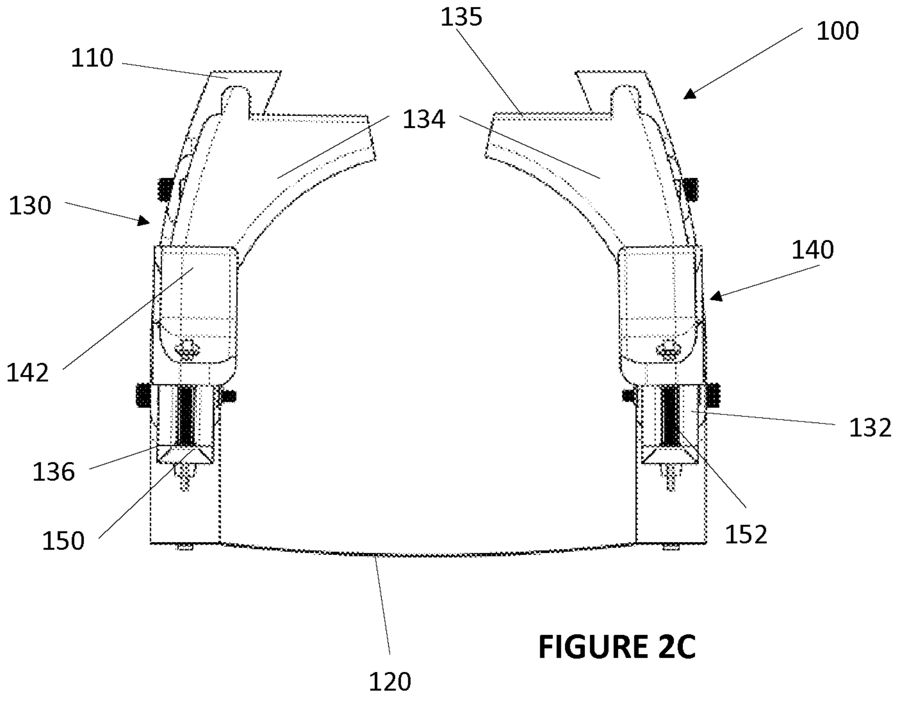
FIG. 2C is a top view planar illustration of the skeletal structure of FIGS. 1A-1B.

FIGS. 1A and 1B are front and back perspective view illustrations of a skeletal structure 100 of a sleep-apnea treatment device according to an embodiment of the disclosed technology. FIGS. 2A to 2E are, respectively, front, back, top, bottom, and side view planar illustrations of skeletal structure 100. FIG. 3 is a perspective illustration of adjustable portions of skeletal structure 100.

Skeletal structure 100 includes a lower section 102 and an upper section 104, the upper and lower sections being connected by rods 106 disposed near the front of the skeletal structure and rods 108 disposed near the back of the skeletal structure.

Lower section 102 of skeletal structure 100 includes two base portions 110, each including a front leg 112, a rear leg 114, and a longitudinal body 115 extending between the front leg 112 and the rear leg 114. Body 115 defines a seat for receiving one of rods 106, and a seat for receiving one of rods 108. In some embodiments, each of the seats extends above body 115, and is surrounded by a collar portion 119.

A rear strip 120, forming a back of the lower section 102, is attached to rear surfaces of rear legs 114, for example by fasteners such as screws. As explained in further detail hereinbelow, rear strip 120 forms part of a neck rest of the sleep-apnea treatment device. In some embodiments, rear strip 120 may be formed of spring steel, allowing for adjustability to a variety of neck circumferences.

Figure 2D:
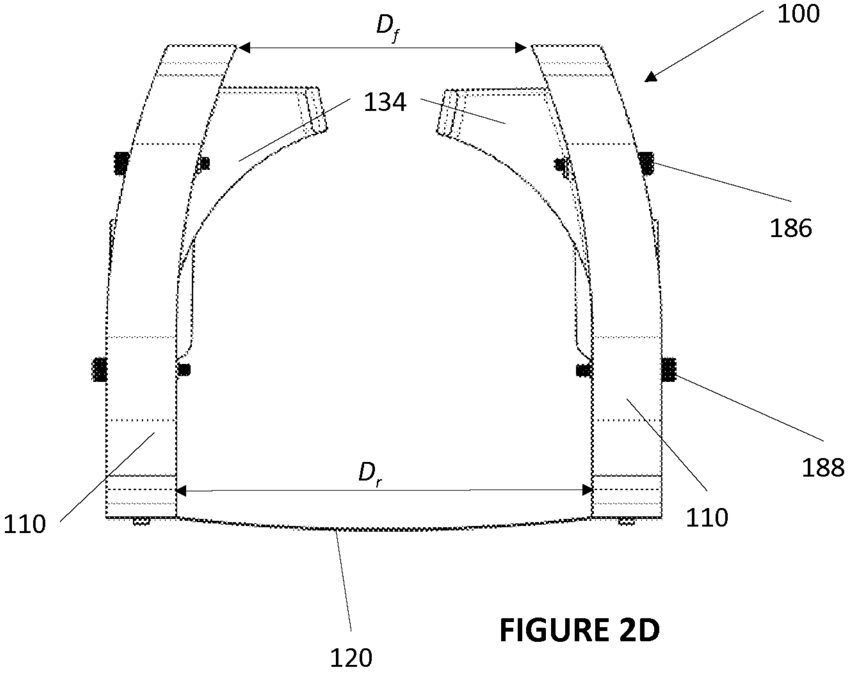
FIG. 2D is a bottom view planar illustration of the skeletal structure of FIGS. 1A-1B.
Figure 3:
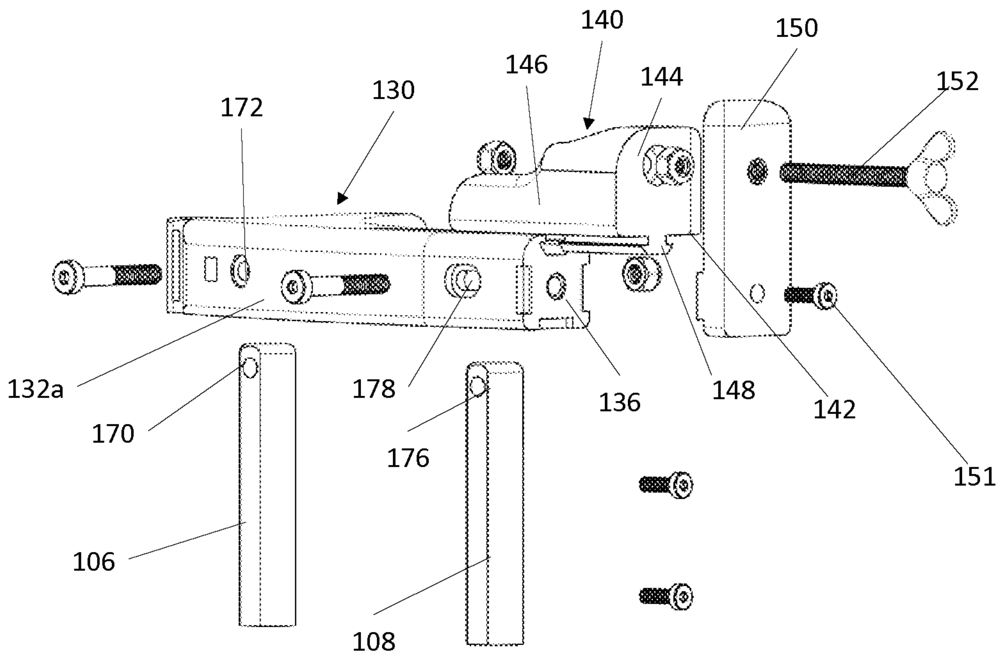
FIG. 3 is a perspective illustration of adjustable portions of the skeletal structure of FIGS. 1A-2E according to an embodiment of the disclosed technology.

As seen clearly in FIG. 2D, base portions 110 extend generally along a front-to-back axis of the skeletal structure, and are not parallel to one another. In some embodiments, a distance Df between front legs 112 is smaller than a distance Dr between rear legs 114. In some embodiments, when viewed from the bottom or from the top, body 115 of each of base portions 110 curves from rear leg 114 toward front leg 112.

For purposes of the present specification and claims, the term "generally" is defined as "according to what an average observer would call as such." Thus, "generally along front-to-back axis" is defined as what an average person would call "front-to-back", or within a 10% tolerance level of geometrical front-to-back. Similarly, "generally planar" and "generally parallel" are defined as what an average person would call "planar" or "parallel", or within 10% tolerance level of geometrically planar or geometrically parallel.

Upper section 104 of skeletal structure 100 includes a pair of supports 130, adapted to support the user's jaw and/or chin. As seen in the Figures, each support 130 includes a body portion 132, which is elongate. Body portion 132 may be linear, or may have a slight curvature, as seen for example in FIG. 2C. A generally planar support shelf 134 extends from body portion 132, and terminates at a front end 135 of the body portion. Hook and loop fastener, or another temporary fastening mechanism, can be used to hold together, bring closer, and/or attach the two planar support shelves 134 on opposing sides of skeletal structure 100. A remainder of body portion 132, rearward of support shelf 134, terminates in a rear surface 136.

Supports 130 extend generally along a front-to-back axis of skeletal structure 100, with support shelves 134 jutting inwardly from the supports toward the center of skeletal structure 100, generally parallel to a base surface of the skeletal structure.

In some embodiments, a longitudinal rail 138 may be formed in body portion 132, rearwardly of support shelf 134, as shown clearly in FIG. 2C. In some embodiments, rail 138 may be in the form of a longitudinal cutout or recess in the body portion 132. In other embodiments, rail 138 may extend outwardly from body portion 132.

Upper section 104 further includes a pair of jaw-pushing elements 140. Each jaw-pushing element 140 includes a lower surface 142, a rear surface 144, and a single side surface 146. In some embodiments, and as shown in FIG. 3, a longitudinal rail 148 is formed in, or extends outwardly from, lower surface 142 of the jaw-pushing element.

Each jaw-pushing element 140 is disposed above a corresponding body portion 132, and is slidable relative thereto along part of the length of the body portion. For example, in some embodiments, longitudinal rail 148 is sized and configured to be complementary to longitudinal rail 138 of the body portion 132 of the corresponding support 130, to facilitate motion of the jaw-pushing element relative to the support.

As shown clearly in FIGS. 1A-1B, side surface 146 of each jaw-pushing element is disposed along the exterior surface 132*a* of body portion 132, distal to the corresponding support shelf 134.

Each support 130 has a rear mounting bracket 150 fixedly attached to rear surface 136 of body portion 132, for example by a fastener 151, shown in FIG. 3. Additionally, rear surface 144 of jaw-pushing element 140 is attached to rear mounting bracket 150 by a threaded connection, such as a threaded rod 152. Rotation of threaded rod 152 moves jaw-pushing element 140 relative to rear mounting bracket 150 along the length of body portion 132, for example along rail 138 thereof.

Rods 106 and 108 connect lower section 102 and upper section 104 of skeletal structure 100.

A lower end of each rod 106 is received within a corresponding seat in one of base portions 110. Additionally, and as shown in FIG. 3, an upper end of each rod 106 includes a bore 170. Rod 106 is adapted to fit into a bore formed in body portion 132, adjacent front end 135 thereof, and corresponding in location to a bore 172 formed in exterior surface 132*a*. A position of the upper end of rod 106 can be adjusted relative to support 130 using a suitable adjustment mechanism, that can include a hinge joint.

In some embodiments, the adjustment mechanism can facilitate adjustment of position of rod 106 relative to support 130 to change a vertical distance between base portion 110 and support 130. In some embodiments, the adjustment mechanism can facilitate adjustment of an angular orientation of rod 106 relative to support 130, thereby changing an angular orientation between base portion 110 and support 130.

In a similar manner, a lower end of each rod 108 is received within a corresponding seat in one of base portions 110. Additionally, an upper end of each rod 108 includes a bore 176. Rod 108 is adapted to fit into a bore formed in body portion 132, adjacent rear surface 136 thereof and corresponding in location to a bore 178 formed in exterior surface 132*a*. A position of the upper end of rod 108 can be adjusted relative to support 130 using an adjustment mechanism, that can include a hinge joint.

In some embodiments, the adjustment mechanism can facilitate adjustment of position of rod 108 relative to support 130 to change a vertical distance between base portion 110 and support 130. In some embodiments, the adjustment mechanism can facilitate adjustment of an angular orientation of rod 108 relative to support 130, thereby changing an angular orientation between base portion 110 and support 130.

Figure 2E:
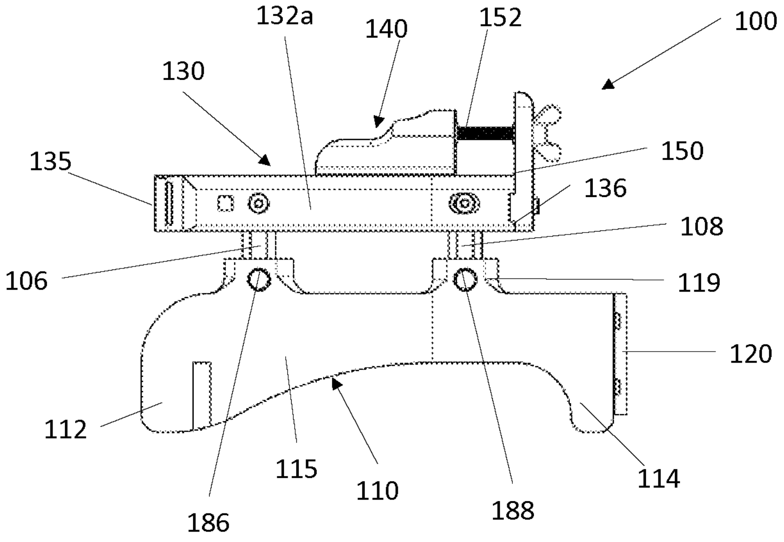
FIG. 2E is a side view planar illustration of the skeletal structure of FIGS. 1A-1B.

In some embodiments, anchoring of rods 106 and/or 108 within corresponding seats of base portions 110 may be tightened by corresponding fasteners 186 and/or 188, shown for example in FIG. 2E. In some embodiments, fasteners 186 and/or 188 may function as adjustment mechanisms, facilitating adjustment of a lower portion of rods 106 and/or 108 relative to corresponding seats.

In some embodiments, components of skeletal structure 100 are each formed of a carbon-fiber based material such as carbon-fiber nylon. In some embodiments, components of skeletal structure 100 that engage the body of the user, such as supports 130 and jaw-pushing elements 140 may be coated with a cushioning and/or comfort material layer. For example, the coating may be, or may include, foam and/or faux leather or a cooling material, for example as found in headphones.

Figure 4:
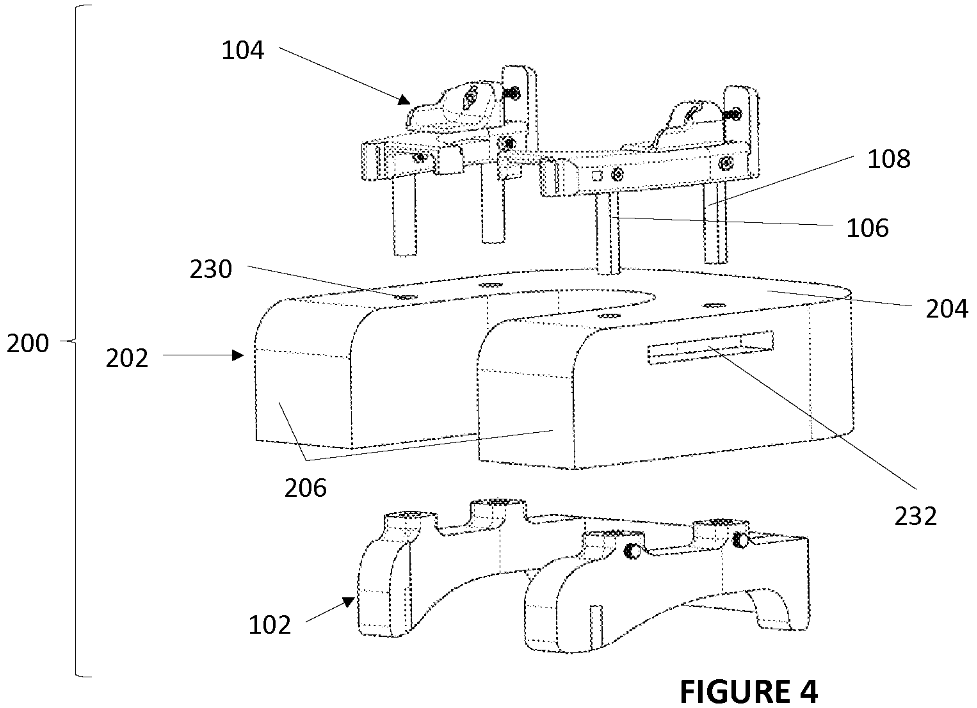
FIG. 4 is a partially exploded perspective view illustration of a sleep-apnea treatment device according to an embodiment of the disclosed technology.

Reference is now made to FIG. 4, which is a partially exploded perspective view illustration of a sleep-apnea treatment device 200 according to an embodiment of the disclosed technology. Sleep-apnea treatment device 200 includes skeletal structure 100 described hereinabove with respect to FIGS. 1A to 3, as well as a cushioning structure 202.

Cushioning structure 202 is generally hoof-shaped, and includes a curved rear portion 204, and two side portions 206, defining a space 208 therebetween.

Side portions 206 extend from left and right sides of rear portion 204, toward a front of cushioning structure 202. Side portions 206 are substantially the same height, and each define an upper surface, a front surface, an outer surface, an inner surface, and a lower surface.

Rear portion 204 has an upper surface, an outer surface, a curved neck-rest surface, and a lower surface. Rear portion 204 is adapted to comfortably support the back of the neck of the user, as explained in further detail hereinbelow.

In some embodiments, a core of cushioning structure 202 is integrally formed. In some embodiments, the cushioning structure includes a foam core, for example memory foam, covered by a second material, such as a cooling polyester covering, similar to the structure found in many headphone sets. In some embodiments, the covering may be removable from the core, to facilitate cleaning of the cushioning structure.

Figure 5A:
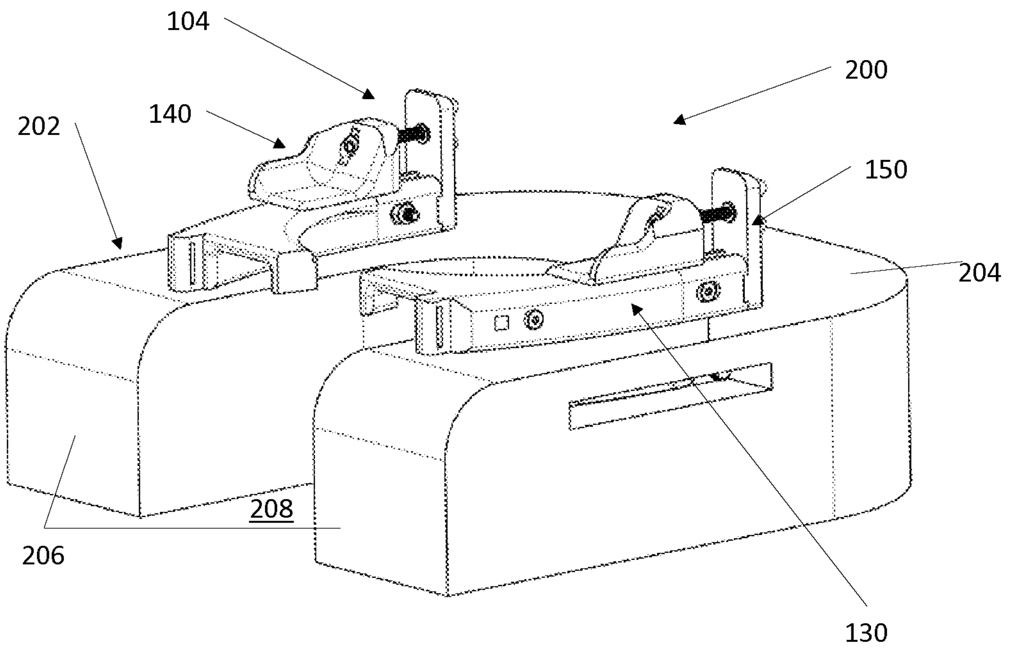
FIG. 5A is a first perspective view illustration of a sleep-apnea treatment device according to embodiments of the disclosed technology.
Figure 5B:
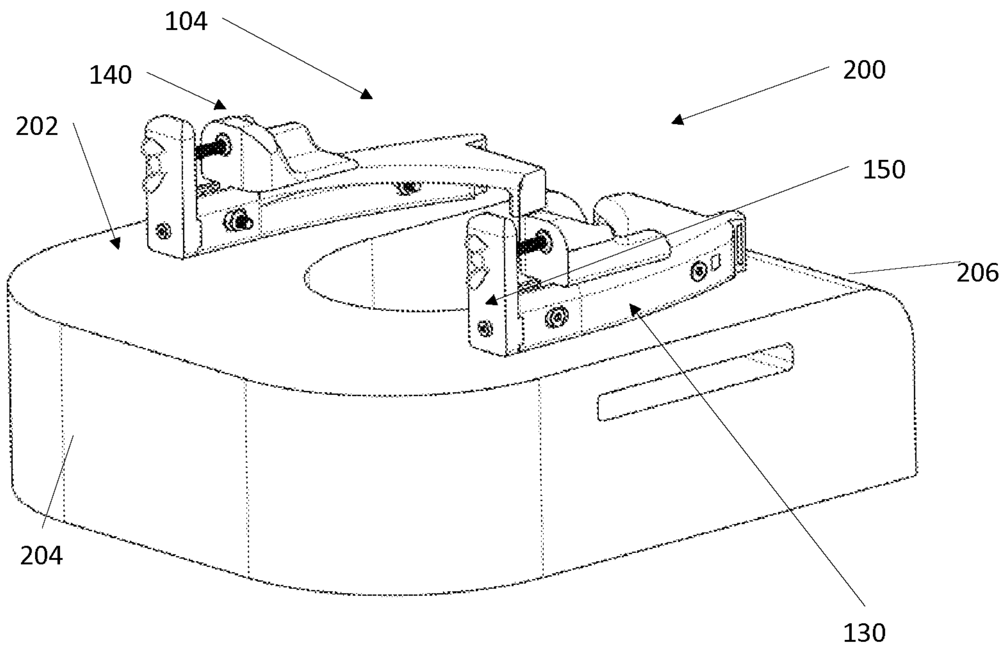
FIG. 5B is a second perspective view illustration of the sleep-apnea treatment device of FIG. 5A.
Figure 5C:
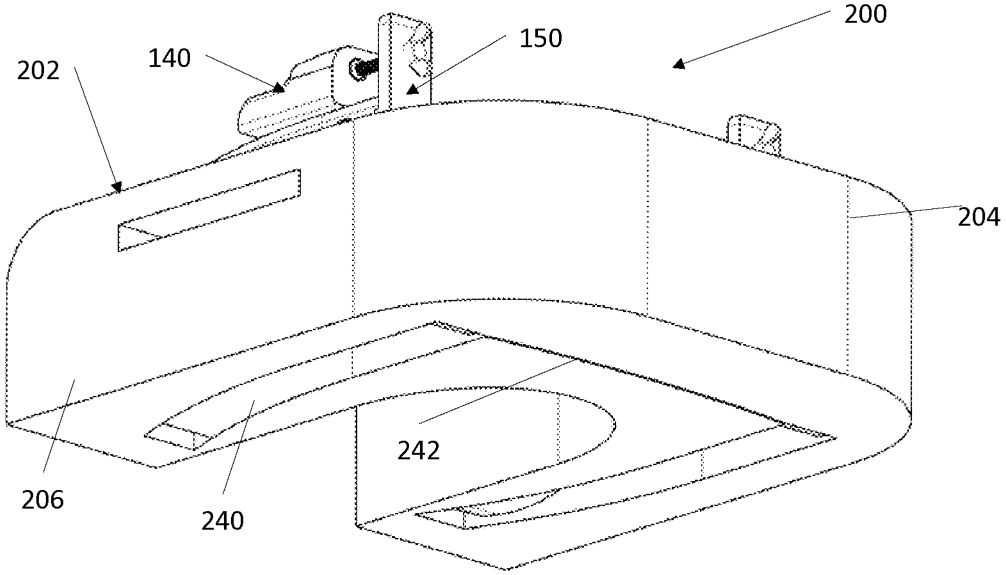
FIG. 5C is a third perspective view illustration of the sleep-apnea treatment device of FIG. 5A.
Figure 6A:
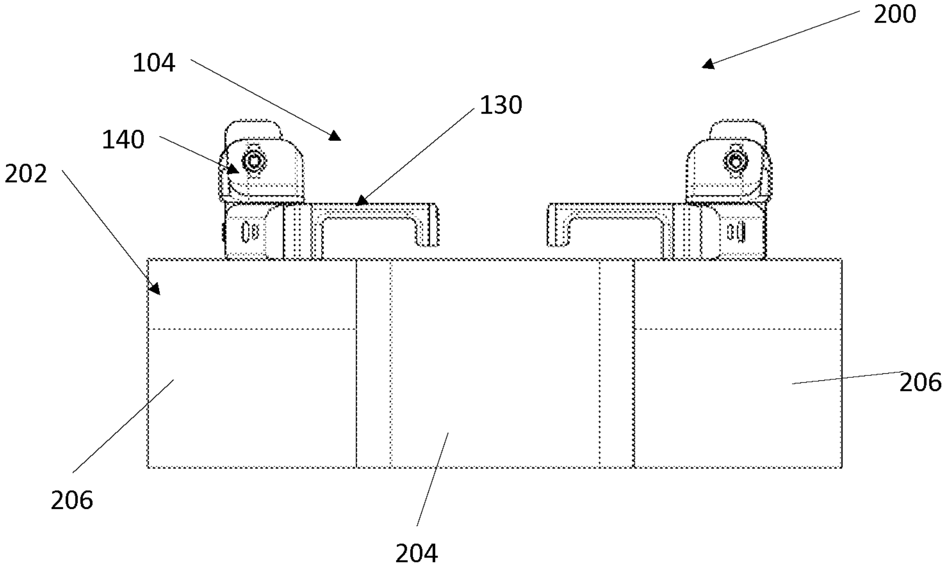
FIG. 6A is a front view planar illustration of the sleep-apnea treatment device of FIGS. 5A-5C.
Figure 6B:
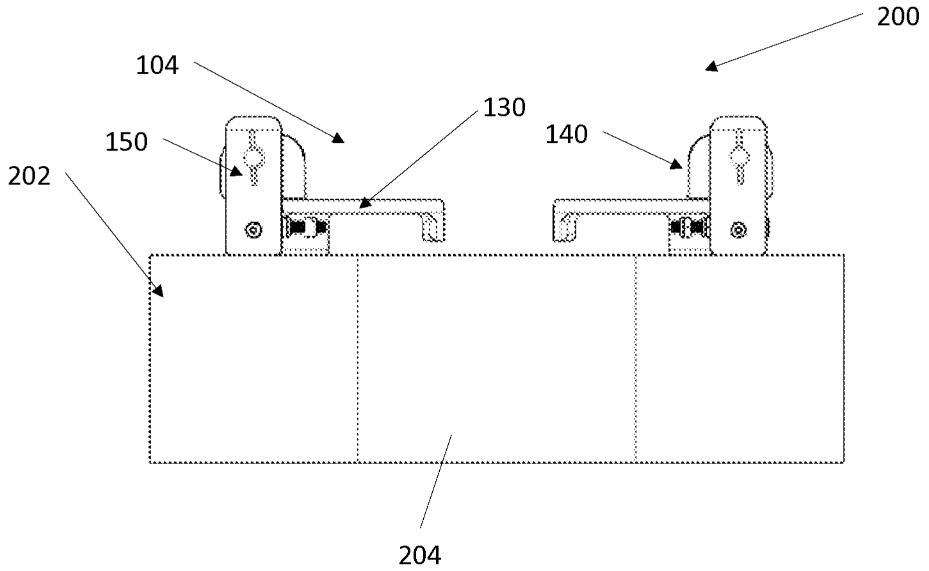
FIG. 6B is a back view planar illustration of sleep-apnea treatment device of FIGS. 5A-5C.
Figure 6C:
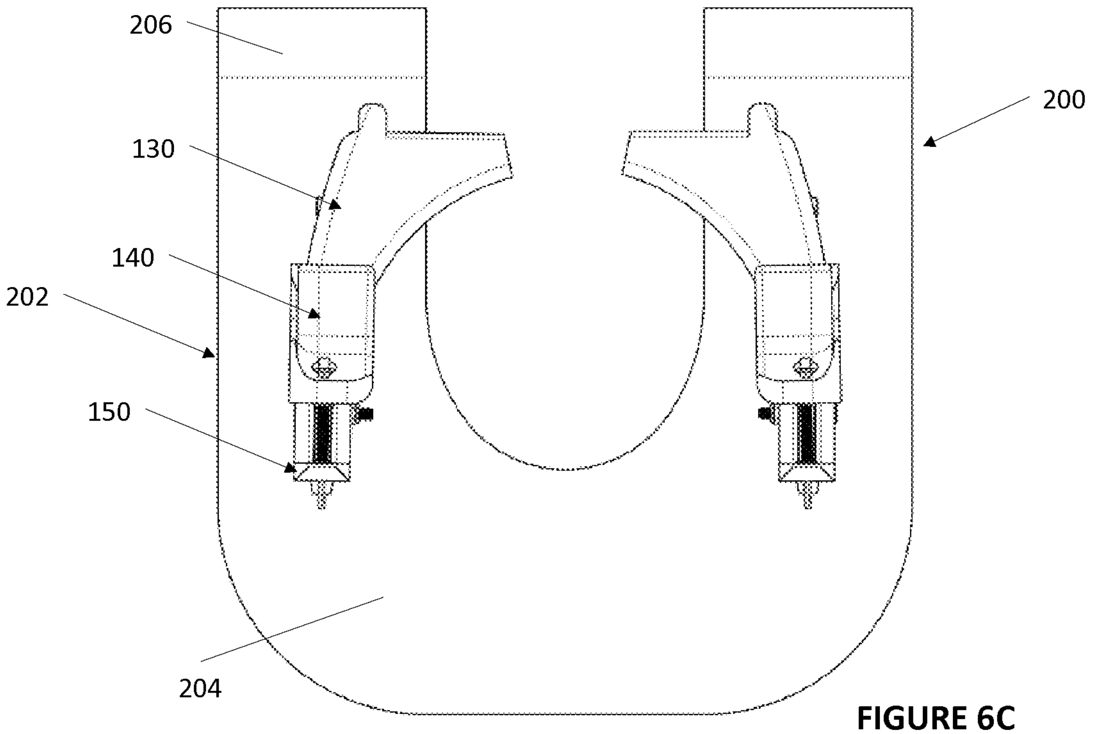
FIG. 6C is a top view planar illustration of the sleep-apnea treatment device of FIGS. 5A-5C.
Figure 6D:
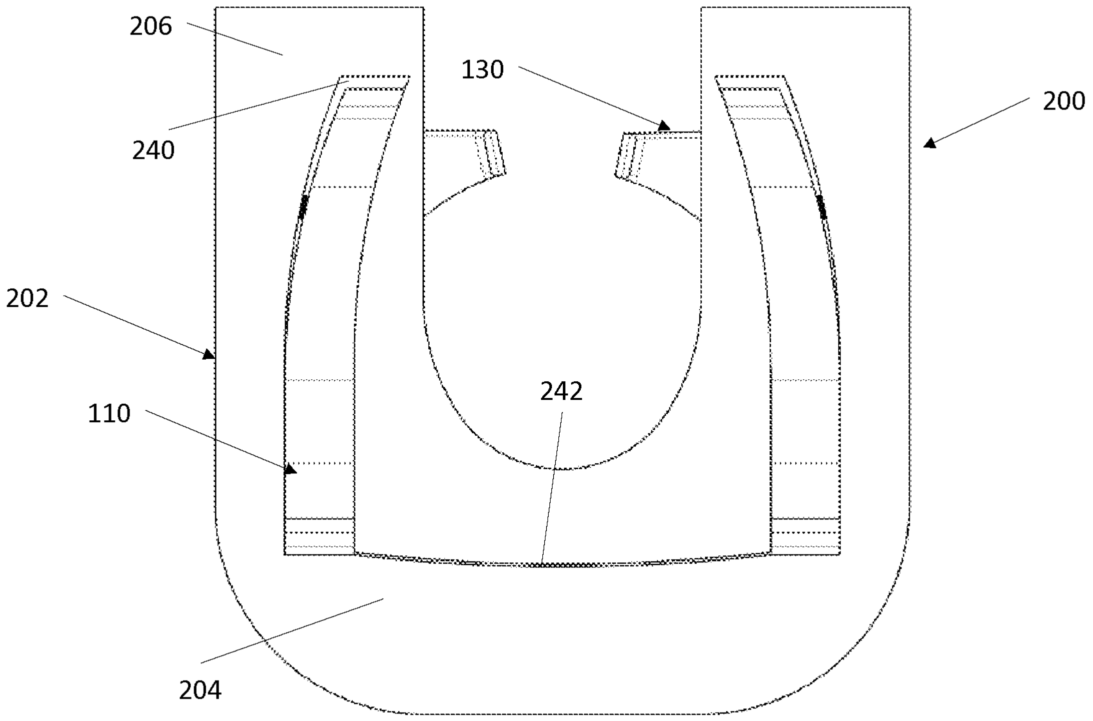
FIG. 6D is a bottom view planar illustration of the sleep-apnea treatment device of FIGS. 5A-5C.
Figure 6E:
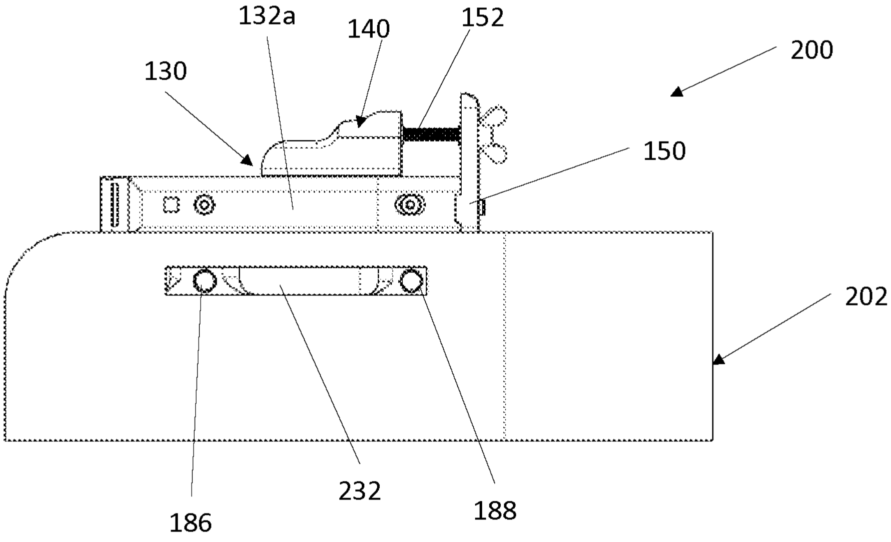
FIG. 6E is a side view planar illustration of the sleep-apnea treatment device of FIGS. 5A-5C.

As explained in further detail hereinbelow, and as shown in FIG. 5C, cavities are formed within rear portion 204 and within side portions 206 to receive lower section 102 of skeletal structure 100 of the sleep-apnea treatment device. Additionally, longitudinal bores 230 are formed within side portions 204, which bores extend through the upper surfaces of the side portions 206, to facilitate extension of rods 106 and 108 out of cushioning structure 202. Furthermore, slots 232 may be formed in the outer surfaces of side portions 206, to facilitate access to fasteners 186 and/or 188 of the skeletal structure.

It is to be appreciated that in some embodiments, cushioning structure 202 may have a different exterior shape. For example, in some embodiments, rear portion 204 may be higher than side portions 206, with a vertical or curved surface connecting the upper surfaces of the rear and side portions. Any configuration of cushioning structure 202 is considered within the scope of the disclosed technology, provided that it facilitates receipt of the skeletal structure as described herein.

Reference is now additionally made to FIGS. 5A, 5B, and 5C, which are perspective view illustrations of sleep-apnea treatment device 200, and to FIGS. 6A, 6B, 6C, 6D, and 6E, which are, respectively, front, back, top, bottom, and side view planar illustration of sleep-apnea treatment device 200.

As seen, upper section 104 of skeletal structure 100, including supports 130, jaw-pushing elements 140, and mounting brackets 150 are disposed outside of cushioning structure 202. Typically, the majority of upper section 104 of the skeletal structure is disposed forwardly to rear portion 204 of the cushioning structure. Supports 130 are generally disposed above the upper surfaces of side portions 206 of cushioning structure 202.

Lower section 102 of skeletal structure 100 is disposed within cushioning structure 202. As shown clearly in FIGS. 5C and 6D, base portions 110 are disposed within cavities 240 in side portions 206, and rear strip 120 is disposed within a slot 242 in rear portion 204. Rods 106 and 108 extend through longitudinal bores 230, to connect base portions 110 within cushioning structure 202 with supports 130 disposed above the cushioning structure.

It is to be appreciated that threaded rod 152, or another mechanism for moving jaw-pushing elements 140 relative to supports 130, and adjustment mechanisms 174 and 180 are disposed outside of cushioning structure 202 and are accessible to the user for adjustment of the fit of device 200, as explained in further detail hereinbelow with respect to FIG. 7. Furthermore, fasteners 186 and/or 188 are accessible via slots 232 to facilitate tightening or adjustment of a connection between rods 106 and/or 108 and base portions 110, if necessary.

Figure 7:
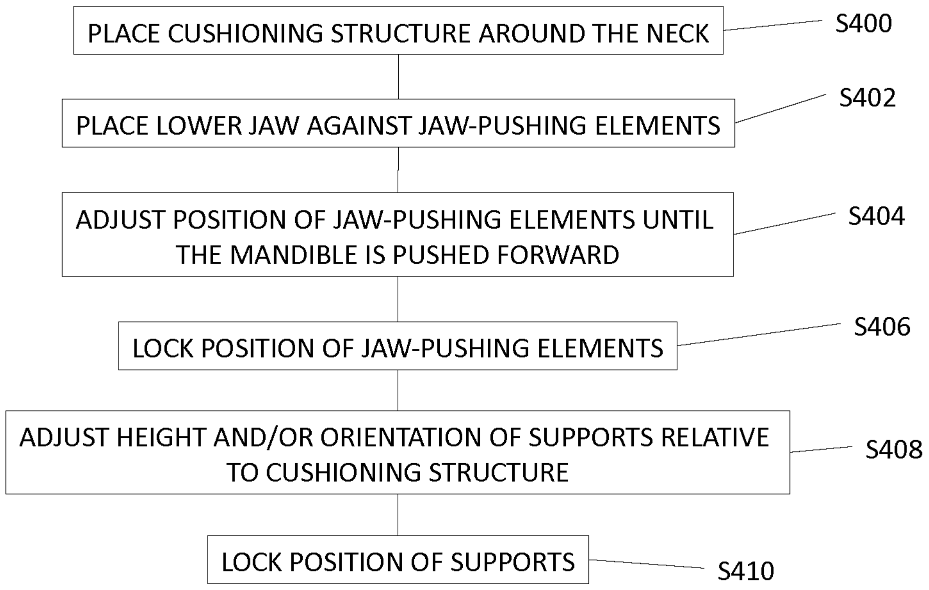
FIG. 7 is a flow chart of a method of use of the sleep-apnea treatment device of FIGS. 5A-6E according to embodiments of the disclosed technology.

Reference is now made to FIG. 7, which is a flow chart of a method of use of sleep-apnea treatment device 200 of FIGS. 5A to 6E according to embodiments of the disclosed technology.

When the user wishes to don the device (e.g., before going to sleep), at step S400, the user places cushioning structure 200 around their neck such that the back of the user's neck rests against neck-rest surface 224 of rear portion 204, and side portions 206 extend on either side of the user's neck.

At step S402, the user places their lower jaw against jaw-pushing elements 140, such that their mandible is supported by support shelves 134 of supports 130. Subsequently, at step S404, the user can adjust the position of jaw-pushing elements 140 relative to supports 130, for example using threaded rods 152, until the user's mandible is pushed sufficiently forward to pull the tongue away from the throat. At step S406, the user ensures that the established position of jaw-pushing elements relative to supports 130 is locked, or secured.

In some embodiments, at step S408, the user adjusts the height and/or orientation of supports 130 relative to base portions 110 and to cushioning structure 202 using adjustment mechanisms 174 and/or 180. Such adjustment may be required to ensure that the user's mandible is lifted upward, extending the neck and increasing space in the throat. Typically, though not necessarily, the adjustment is mostly an adjustment of the orientation of rods 106. At step S410 the user ensures that the position of supports 130 relative to base portions 110, established in step S408, is locked, or secured.

Once steps S400 to S410 are completed, the user can lie down or go to sleep, wearing device 200 around their neck, and know that their mandible, neck, and tongue are positioned to reduce or prevent sleep apnea.

Any device or step to a method described in this disclosure can comprise or consist of that which it is a part of, or the parts, which make up the device or step. The term "and/or" is inclusive of the items which it joins linguistically and each item by itself. "Substantially" is defined as "at least 95% of the term being described and up to 100%" and any device or aspect of a device or method described herein can be read as "comprising" or "consisting" thereof.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

I claim:

1. A sleep apnea device for positioning the neck and jaw of a user, the device comprising:

(a) a skeletal structure including:

a lower section;

an upper section including at least one support adapted to support the jaw of a user; and a plurality of longitudinal rods, each rod of the plurality of longitudinal rods directly connecting the lower section and the upper section; and (b) a curved cushioning structure including a rear portion and side portions, the cushioning structure defining at least one cavity on a bottom side thereof, a plurality of longitudinal bores extending from a top to the bottom of the curved cushioning structure, and the top of the curved cushioning structure having an upper surface, wherein the lower section of the skeletal structure is disposed within the at least one cavity of the cushioning structure, the upper section of the skeletal structure is disposed above the upper surface of the cushioning structure, and each longitudinal rod in the plurality of longitudinal rods extends through a corresponding one of the plurality of longitudinal bores to connect the upper section of the skeletal structure with the lower section of the skeletal structure.

2. The device of claim 1, wherein the lower section includes a pair of base portions connected to each other by a rear strip, the rear strip forming right angles with the base portions, the base portions and the rear strip being disposed within the at least one cavity of the cushioning structure, each of the base portions including a raised seat for a lower end of at least one of the plurality of rods.

3. The device of claim 2, wherein the at least one cavity comprises a longitudinal cavity defined in each of the side portions of the cushioning structure and a slit defined in the rear portion of the cushioning structure, each longitudinal cavity accommodating an entirety of one of the base portions and the slit accommodating an entirety of the rear strip.

4. The device of claim 3, wherein the plurality of longitudinal bores in the cushioning structure extend between the longitudinal cavities and the upper surface of the cushioning structure.

5. The device of claim 1, wherein the upper section includes:

- a pair of supports, each including:
  - a body; and
  - a support shelf extending inwardly from the body and adapted to support the jaw of the user; and
- a pair of jaw-pushing elements, each associated with one of the supports and movable relative thereto, the jaw-pushing elements adapted, when the device is worn around the neck of the user, to cup the jaw of the user and to position the jaw relative to the neck of the user to improve air flow during sleep.

6. A method of treating obstructive sleep apnea using the device of claim 5, the method comprising:

- placing the cushioning structure around the neck of the user;
- placing the mandible within the jaw-pushing elements; and
- adjusting a position of the jaw pushing elements relative to the corresponding supports, to ensure that the mandible is pushed forward and pulls the tongue away from the user's throat.

7. The method of claim 6, further comprising adjusting an angle of the supports relative to the upper surface of the cushioning structure to ensure that the mandible is lifted upward and the neck of the user is extended to increase the space in the throat.

8. The device of claim 1, wherein a connection between the plurality of longitudinal rods and the upper section of the skeletal structure is adjustable to modify an angle of the upper section relative to the lower section of the skeletal structure such that, when the device is worn around the neck of the user, the neck of the user is extended to improve air flow during sleep.

9. The sleep apnea device for positioning the neck and jaw of a user of claim 1, wherein:

- rods of the plurality of rods are disposed near the front of the skeletal structure; and
- rods of the plurality of rods are disposed near the back of the skeletal structure.

* * * * *